(12) United States Patent
Usui et al.

(10) Patent No.: US 10,365,250 B2
(45) Date of Patent: Jul. 30, 2019

(54) DETECTION DEVICE, DETECTION SYSTEM, AND DETECTION METHOD

(71) Applicant: KABUSHIKI KAISHA TOSHIBA, Tokyo (JP)

(72) Inventors: Takashi Usui, Saitama (JP); Kazuo Watabe, Kanagawa (JP); Takahiro Omori, Kanagawa (JP); Hidefumi Takamine, Tokyo (JP); Akihiro Kasahara, Chiba (JP)

(73) Assignee: Kabushiki Kaisha Toshiba, Tokyo (JP)

(*) Notice: Subject to any disclaimer, the term of this patent is extended or adjusted under 35 U.S.C. 154(b) by 177 days.

(21) Appl. No.: 15/264,206

(22) Filed: Sep. 13, 2016

(65) Prior Publication Data
US 2017/0138910 A1    May 18, 2017

(30) Foreign Application Priority Data
Nov. 12, 2015 (JP) .................................. 2015-222376

(51) Int. Cl.
*G01N 29/04* (2006.01)
*G01N 29/07* (2006.01)
(Continued)

(52) U.S. Cl.
CPC ........... *G01N 29/226* (2013.01); *G01N 29/04* (2013.01); *G01N 29/043* (2013.01); *G01N 29/07* (2013.01);
(Continued)

(58) Field of Classification Search
CPC .... G01N 29/226; G01N 29/04; G01N 29/046; G01N 29/14; G01H 13/00
(Continued)

(56) References Cited

U.S. PATENT DOCUMENTS 4,535,629 A * 8/1985 Prine ...................... G01N 29/14
702/39
4,549,437 A * 10/1985 Weins .................... G01N 29/14
73/587
(Continued)

FOREIGN PATENT DOCUMENTS

CN          10399505 A  *  8/2014  ............. G01N 29/04
JP      2003-315317         11/2003
(Continued)

OTHER PUBLICATIONS

Uchima et al. (2009). "U-rib stagnant water diagnosis of steel deck by thermal infrared measurement method," *Japan Society of Civil Engineers, The 64th Annual Meeting Pamphlet*, VI-340: pp. 679-680.

*Primary Examiner* — Justin Seo
*Assistant Examiner* — Rose M Miller
(74) *Attorney, Agent, or Firm* — Finnegan, Henderson, Farabow, Garrett & Dunner, L.L.P.

(57) ABSTRACT

According to an embodiment, a detection device is used for a structure. The structure includes: a first member; a second member provided on an opposite side of the first member; and a welded portion that is provided along an end of the second member facing the first member and fixes the first member and the second member. The detection device include: a plurality of acoustic emission sensors that are disposed so as to be spaced apart from each other in a direction in which the welded portion extends and are configured to detect an elastic wave transmitted to the second member, each acoustic emission sensor being attached to the second member; and an outputter that outputs information, obtained from outputs of the plurality of the acoustic emission sensors.

19 Claims, 10 Drawing Sheets

(51) Int. Cl.
*G01N 29/14* (2006.01)
*G01N 29/22* (2006.01)

(52) U.S. Cl.
CPC ............ *G01N 29/14* (2013.01); *G01N 29/223* (2013.01); *G01N 2291/0258* (2013.01); *G01N 2291/106* (2013.01); *G01N 2291/267* (2013.01)

(58) Field of Classification Search
USPC .......................................... 73/645, 587, 646
See application file for complete search history.

(56) References Cited

U.S. PATENT DOCUMENTS

| | | | | |
|---|---|---|---|---|
| 4,901,575 A | * | 2/1990 | Bohannan | ................ G01H 1/00 73/587 |
| 4,956,999 A | * | 9/1990 | Bohannan | ................ G01H 1/00 73/587 |
| 5,457,994 A | * | 10/1995 | Kwun | ................... G01N 29/14 73/587 |
| 2009/0070048 A1 | | 3/2009 | Stothers et al. | |
| 2016/0139084 A1 | | 5/2016 | Usui et al. | |
| 2016/0282310 A1 | | 9/2016 | Usui et al. | |

FOREIGN PATENT DOCUMENTS

| | | |
|---|---|---|
| JP | 2004-61432 | 2/2004 |
| JP | 2007-047094 A | 2/2007 |
| JP | 2009-014513 A | 1/2009 |
| JP | 2010-54497 | 3/2010 |
| JP | 2010-133835 | 6/2010 |
| JP | 2011-102700 | 5/2011 |
| JP | 2014-095555 A | 5/2014 |
| JP | 2016-99119 | 5/2016 |
| JP | 2016-180598 | 10/2016 |

* cited by examiner

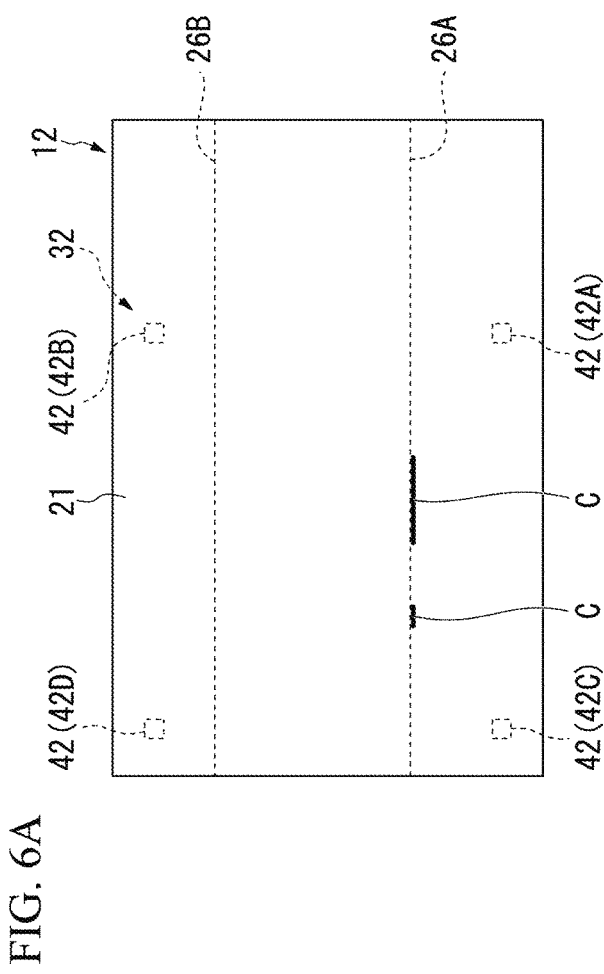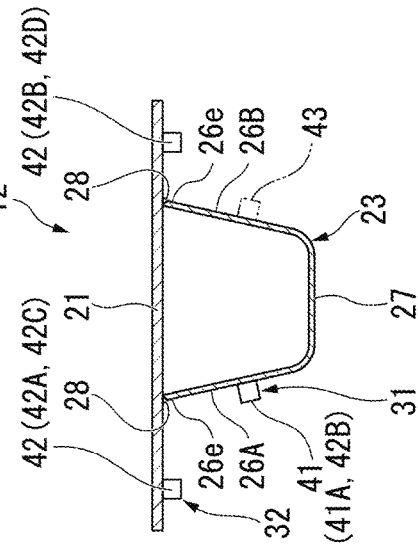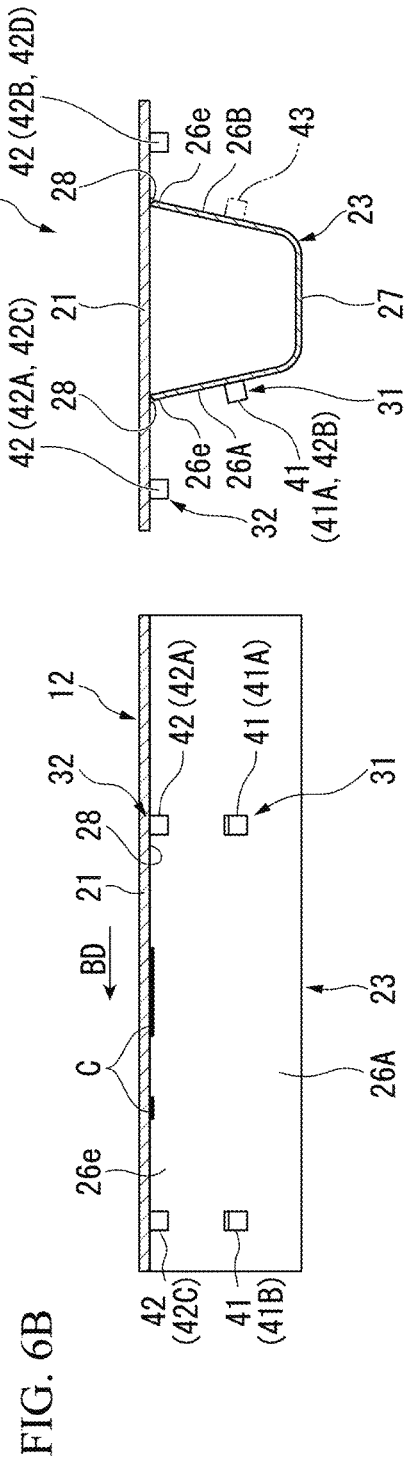

DETECTION DEVICE, DETECTION SYSTEM, AND DETECTION METHOD

CROSS-REFERENCE TO RELATED APPLICATION

This application claims priority from Japanese Patent Application No. 2015-222376 filed on Nov. 12, 2015, the contents of which are incorporated herein by reference in their entirety.

FIELD

Embodiments described herein relate generally to a detection device, a detection system, and a detection method.

BACKGROUND

It has been known that a fatigue crack occurs in a welded portion of a structure such as, for example, a bridge, in association with use of the structure for a long period of time.

Here, various detection methods of detecting a deterioration of a structure have been proposed so far. However, various restrictions are imposed on these detection methods with respect to the installation height, state of the structure, and there may be a case where a crack occurring in the structure cannot be simply detected.

BRIEF DESCRIPTION OF THE DRAWINGS

FIGS. 6A to 6C are diagrams showing an arrangement example of AE sensors of the embodiment.

DETAILED DESCRIPTION

Figure 1:
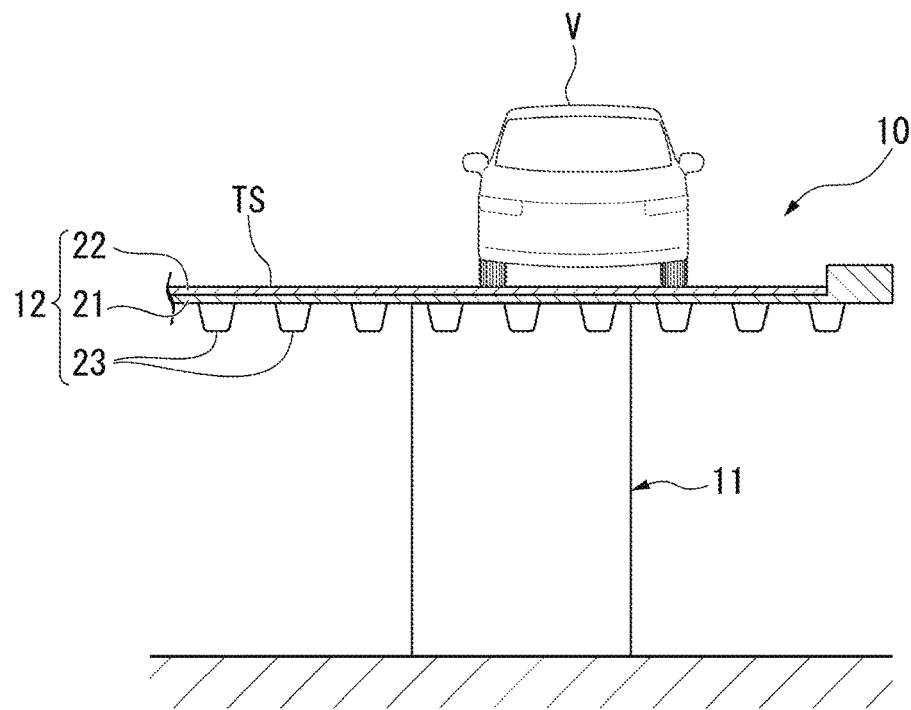
FIG. 1 is a cross-sectional view showing a bridge structure of one embodiment.

According to an embodiment, a detection device is used for a structure. The structure includes: a first member that supports, from below, a traveling surface on which a vehicle travels; a second member provided on an opposite side of the traveling surface with respect to the first member; and a welded portion that is provided along an end of the second member facing the first member, the welded portion fixing the first member and the second member in a continuous manner in a longitudinal direction of the second member. The detection device include: a first plurality of acoustic emission sensors that are disposed so as to be spaced apart from each other in a direction in which the welded portion extends and are configured to detect an elastic wave transmitted to the second member, each acoustic emission sensor being attached to the second member; and an outputter that outputs information, obtained from outputs of the first plurality of the acoustic emission sensors.

Hereinafter, a detection device, a detection system, and a detection method of an embodiment will be described with reference to the accompanying drawings. Moreover, in the following description, the configurations having the same or similar functions will be assigned by the same reference numerals. Redundant descriptions may be omitted.

One embodiment will be described with reference to FIGS. 1 to 15.

A detection system 1, a detection device 2, and a detection method of the embodiment are used to detect the state of a structure. Particularly, the wording "state of a structure" referred to in the embodiments is used in a broad meaning inclusive of the state of deterioration, the state of a crack, or the like. That is, the wording "detecting the state of a structure" referred to in the embodiments means detecting at least one of the presence or absence of deterioration, the degree of the deterioration, the presence or absence of a crack, the position of the crack, the degree of the crack, and the like. Herein, first, an example of a structure to which the detection system 1, the detection device 2, and the detection method of the embodiment are applied will be described.

FIG. 1 is a cross-sectional view showing an example of a bridge structure 10.

The bridge structure 10 is an example of a "structure" to which the detection system 1, the detection device 2, and the detection method of the embodiment are applied. Particularly, the term "bridge" referred to in the embodiments is not limited to a structure provided on a river, a valley or the like, and widely covers various structures (for example, elevated bridges of an expressway) and the like which are provided further upward than the ground surface. In addition, the structure to which the detection system 1, the detection device 2, and the detection method of the embodiment can be applied is not limited to a bridge, and may preferably be a structure in which an elastic wave is generated in association with the generation or progress of a crack. That is, the detection system 1, the detection device 2, and the detection method of the embodiment may be applied to, for example, a structure which has nothing to do with a road.

As shown in FIG. 1, the bridge structure 10 includes a main girder 11 and a steel plate deck 12.

The main girder 11 is provided on the ground surface, and stands up in a substantially vertical direction.

The steel plate deck 12 is provided on the main girder 11, and forms a traveling surface TS along which a vehicle V travels. The steel plate deck 12 is supported by the main girder 11 from below, and is disposed at a position higher than the ground surface.

Figure 2:
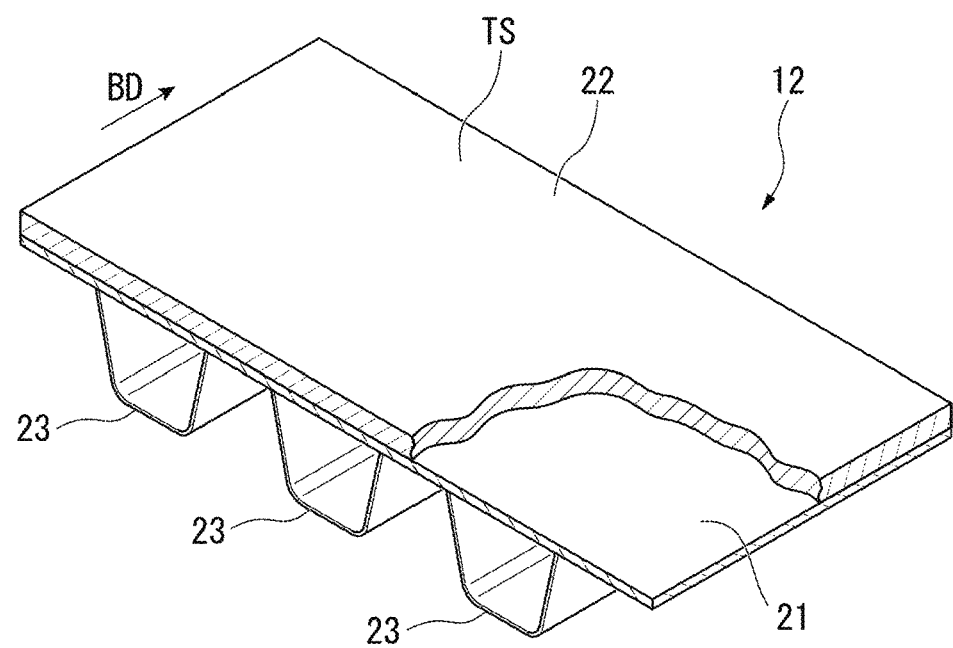
FIG. 2 is a cross-sectional perspective view showing a steel plate deck of the embodiment.

FIG. 2 is a cross-sectional perspective view showing the steel plate deck 12.

Figure 3:
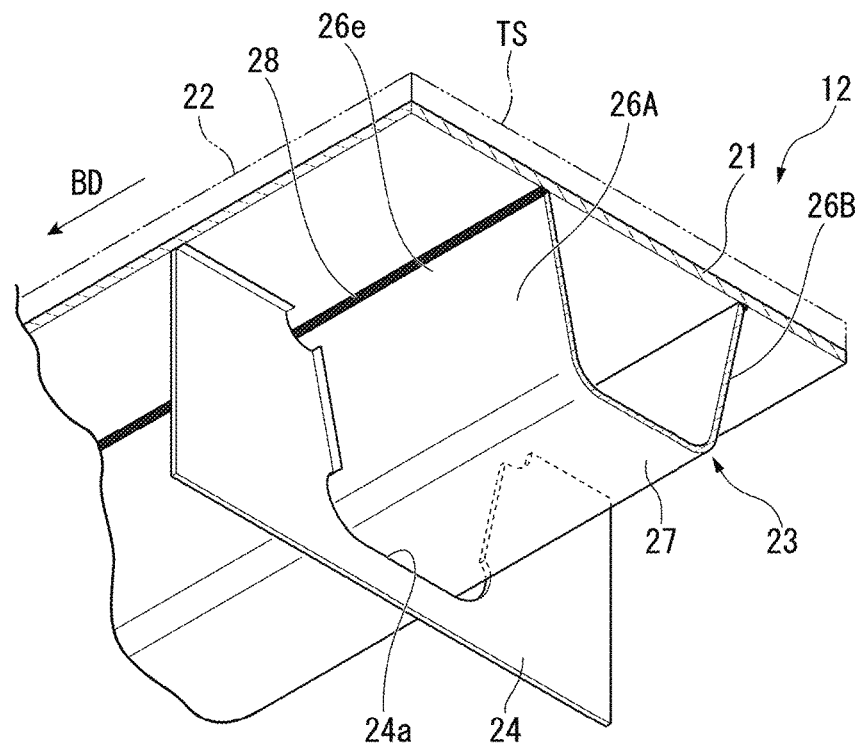
FIG. 3 is a cross-sectional perspective view when the steel plate deck of the embodiment is seen from a different angle.

As shown in FIG. 2, the steel plate deck 12 includes a deck plate 21, a pavement 22, trough ribs (longitudinal ribs) 23, and a lateral rib 24 (see FIG. 3).

The deck plate 21 extends below the traveling surface TS along which the vehicle V travels, and supports the traveling surface TS from below. The deck plate 21 is an example of a "first member". For example, the deck plate 21 is a metallic plate member extending substantially in parallel to the traveling surface TS.

The pavement (pavement member) 22 is provided on the upper surface of the deck plate 21. The pavement 22 is formed of, for example, asphalt or the like. The upper surface of the pavement 22 forms the traveling surface TS along which the vehicle V travels. Particularly, the wording "(the first member) supports the traveling surface from below" referred to in the embodiments includes, for example, the meaning that the first member supports a member (for example, pavement 22) having the traveling surface TS formed thereon from below.

FIG. 3 is a cross-sectional perspective view when the steel plate deck 12 is seen from obliquely downward.

As shown in FIG. 3, the trough rib 23 is provided below the deck plate 21.

That is, the trough rib 23 is provided on the opposite side of the traveling surface TS with respect to the deck plate 21. The trough rib 23 is an example of a "second member". The trough rib 23 is a reinforcement member for reinforcing the deck plate 21. For example, the trough rib 23 is a metallic rib (U rib) having a U-shaped cross-sectional shape. The trough rib 23 is attached to the lower surface of the deck plate 21, and extends along a bridge-axial direction BD. Particularly, the "bridge-axial direction" refers to a direction in which the bridge structure 10 extends, and, for example, a direction along the traveling direction of the vehicle V traveling on the bridge structure 10.

Specifically, the trough rib 23 includes upright standing portions 26A and 26B, and a horizontal portion 27.

Each of a pair of upright standing portions 26A and 26B is a plate portion extending in a direction crossing the traveling surface TS, and extends in a direction away from the traveling surface TS. For example, the pair of upright standing portions 26A and 26B is inclined with respect to each other so that an interval between the upright standing portions 26A and 26B becomes gradually smaller as they extend away from the traveling surface TS. For example, each thickness (plate thickness) of the upright standing portions 26A and 26B is smaller than the thickness (plate thickness) of the deck plate 21. In addition, each thickness (plate thickness) of the upright standing portions 26A and 26B is substantially constant, for example, in the bridge-axial direction BD.

The horizontal portion 27 is a plate which is substantially parallel to the traveling surface TS. The horizontal portion 27 is provided between the lower ends of the pair of upright standing portions 26A and 26B, and connects the lower ends of the upright standing portions 26A and 26B.

The trough rib 23 is formed in a U-shape by the upright standing portions 26A and 26B and the horizontal portion 27 being connected to each other.

On the other hand, the lateral rib 24 is a metallic plate member along a direction (for example, substantially orthogonal to) intersecting the bridge-axial direction BD. The lateral rib 24 includes a cutout 24a through which the trough rib 23 is passed.

For example, the lateral rib 24 is fixed to the lower surface of the deck plate 21 and the lateral sides of the upright standing portions 26A and 26B of the trough rib 23.

Next, a welded portion 28 provided in the steel plate deck 12 will be described.

As shown in FIG. 3, the steel plate deck 12 includes the welded portion 28 between the deck plate 21 and the trough rib 23. Specifically, each of the upright standing portions 26A and 26B of the trough rib 23 includes an end (upper end) 26e facing the deck plate 21. The welded portion 28 is provided along the end 26e of the upright standing portions 26A and 26B of the trough rib 23. The welded portion 28 extends in the bridge-axial direction BD along a direction in which the trough rib 23 extends. The welded portion 28 fixes (joins) the lower surface of the deck plate 21 to the end 26e of the upright standing portions 26A and 26B of the trough rib 23.

Figure 4A:
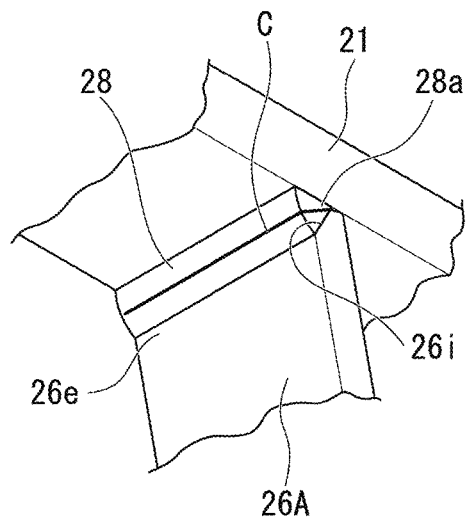
FIGS. 4A and 4B are cross-sectional perspective views showing a welded portion and the periphery of the welded portion of the steel plate deck of the embodiment.
Figure 4B:
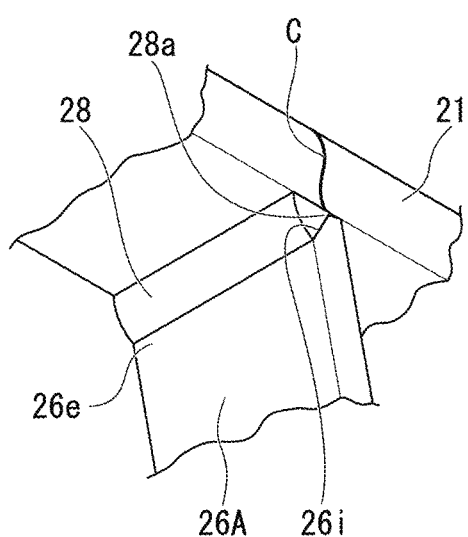

FIGS. 4A and 4B show the welded portion 28 and the periphery of the welded portion 28 of the steel plate deck 12. For convenience of description, hatching performed on cross-section portions is omitted in FIGS. 4A and 4B.

As shown in FIGS. 4A and 4B, the end 26e of the upright standing portions 26A and 26B of the trough rib 23 includes an inclined portion (inclined surface or root surface) 26i. On the end 26e of the upright standing portions 26A and 26B, the inclined portion 26i is provided outside the pair of upright standing portions 26A and 26B. The inclined portion 26i is inclined in a direction away from the lower surface of the deck plate 21 with the progress of the outside of the pair of upright standing portions 26A and 26B. For this reason, a gap into which the welded portion 28 gains entrance is formed between the lower surface of the deck plate 21 and the inclined portion 26i of the upright standing portions 26A and 26B. At least a portion of the welded portion 28 is provided between the lower surface of the deck plate 21 and the inclined portion 26i of the upright standing portions 26A and 26B.

Here, there is the possibility of a fatigue crack C (hereinafter, simply referred to as the crack C) occurring in the welded portion 28 in association with the use of the bridge structure 10 for a long period of time. There are two general patterns in this crack C. As shown in FIG. 4A, the crack C of a first pattern is a crack (bead penetration crack) progressing from a root (root portion) 28a of the welded portion 28 toward a welding bead. On the other hand, as shown in FIG. 4B, the crack C of a second pattern is a crack (deck plate penetration crack) progressing from the root 28a of the welded portion 28 to the deck plate 21. Here, the upper surface of the deck plate 21 is covered by the pavement 22. For this reason, it is particularly difficult to visually confirm the crack C progressing to the deck plate 21.

Next, the detection system 1 of the embodiment will be described.

Figure 5:
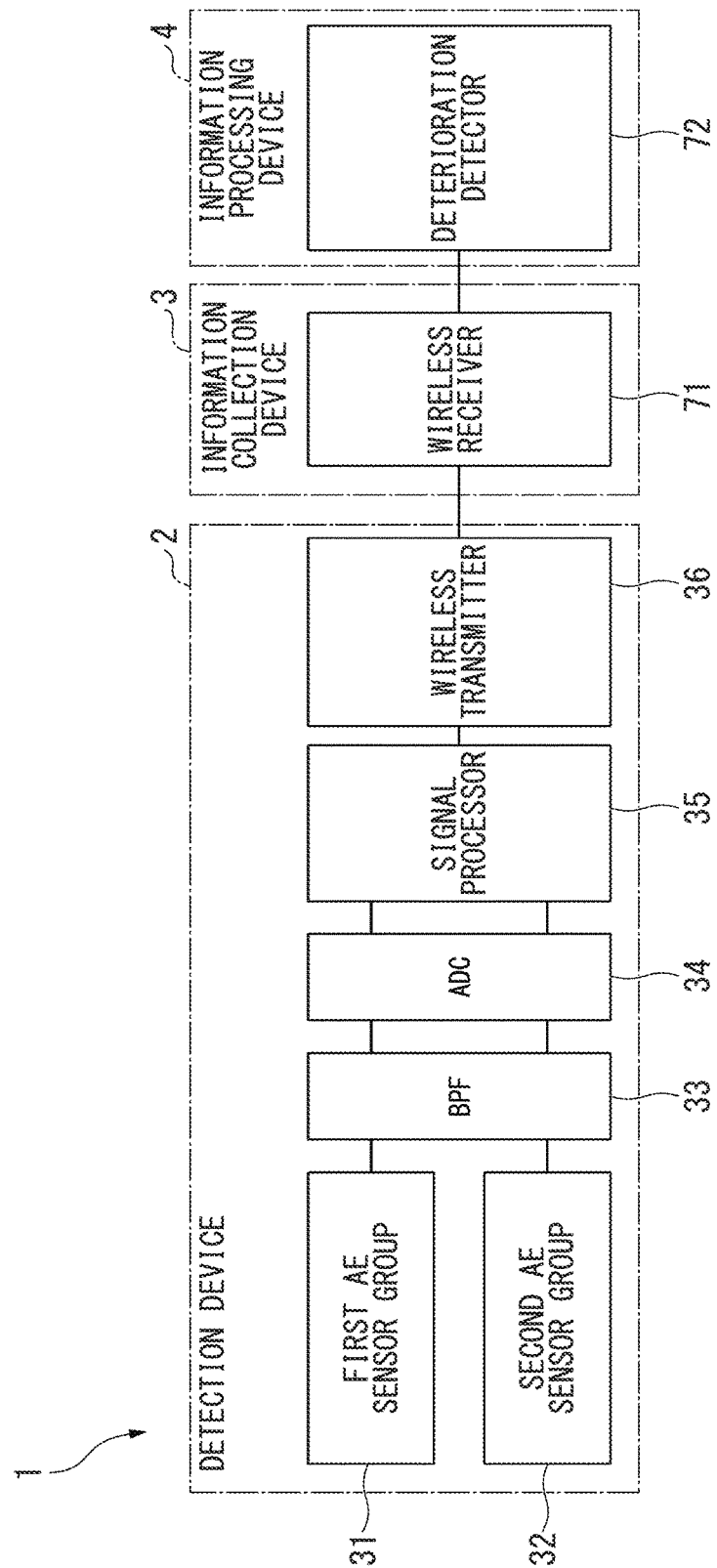
FIG. 5 is a block diagram showing a system configuration of a detection system of the embodiment.

FIG. 5 is a block diagram showing a system configuration of the detection system 1 of the embodiment.

As shown in FIG. 5, the detection system (deterioration detection system or deterioration diagnosis system) 1 includes a detection device 2, an information collection device 3, and an information processing device 4.

First, the detection device 2 will be described.

The detection device 2 is an acoustic emission (AE)-type detection device, provided in the bridge structure 10, which detects an elastic wave occurring in the bridge structure 10.

Particularly, AE refers to a phenomenon in which an elastic wave is generated inside a material in association with the generation of a fatigue crack in the material or the progress of the fatigue crack. The AE-type detection device detects, for example, an elastic wave generated in association with the generation of a fatigue crack in a structure or the progress of the fatigue crack, using a high-sensitive sensor, and detects the state of the structure based on the detected elastic wave.

Specifically, the detection device 2 of the embodiment includes a first AE sensor group 31 (first acoustic emission group), a second AE sensor group 32 (second acoustic emission group), a bandpass filter (BPF) 33, an analog-digital converter (ADC) 34, a signal processor 35, and a wireless transmitter 36.

FIGS. 6A to 6C show an arrangement example of the first and second AE sensor groups 31 and 32. Particularly, FIG. 6A shows a plan view showing the steel plate deck 12. FIG. 6B shows a side view showing the steel plate deck 12. FIG. 6C shows a cross-sectional view showing the steel plate deck 12.

First, the first AE sensor group 31 will be described.

As shown in FIGS. 6A to 6C, the first AE sensor group 31 includes a plurality of AE sensors 41 (acoustic emission sensors). Particularly, the first AE sensor group 31 shown by solid lines in FIGS. 6A to 6C is, for example, a sensor group that detects the crack C of the welded portion 28 provided in one upright standing portion 26A of the trough rib 23. Particularly, a sensor group that detects the crack C of the welded portion 28 provided in the other upright standing portion 26B of the trough rib 23 will be described later. In addition, FIGS. 6A to 6C representatively show two AE sensors 41 included in the first AE sensor group 31. Particularly, the first AE sensor group 31 may include, for example, three or more AE sensors 41 disposed at a predetermined interval in the bridge-axial direction BD.

Here, the AE sensor 41 according to the embodiment will be described.

The AE sensor 41 includes a piezoelectric element, detects an elastic wave (AE wave) transmitted from a generation portion of the crack C, and converts the elastic wave into a voltage signal (AE signal) to output the converted elastic wave. The AE signal is detected as an indication before the fracture of a material occurs. Therefore, the occurrence frequency and signal intensity of the AE signal are useful as an index indicating the soundness of a material. For example, the AE sensor 41 includes a piezoelectric element having sensitivity in a range of 10 kHz to 1 MHz. Particularly, the AE sensor 41 may be any of a resonance type having a resonance peak within the above frequency range, a broadband type having resonance suppressed therein, and the like. In addition, the AE sensor 41 may be a pre-amplifier type having a pre-amplifier built-in, or may be other than this. The detection element itself of the AE sensor 41 may be any of a voltage output type, a resistance change type, and a capacitance type, or may be other than these. Particularly, regarding AE sensors 42 included in the second AE sensor group 32 described later, the configuration and function of the sensor are also the same as those of the AE sensor 41 of the first AE sensor group 31.

As shown in FIGS. 6A to 6C, each of the plurality of the AE sensors 41 included in the first AE sensor group 31 is attached to the trough rib 23. Specifically, each AE sensor 41 is attached to the lateral side of the upright standing portion 26A of the trough rib 23, and is in contact with the upright standing portion 26A. Therefore, each AE sensor 41 detects an elastic wave transmitted from the crack C to the upright standing portion 26A of the trough rib 23.

Figure 8:
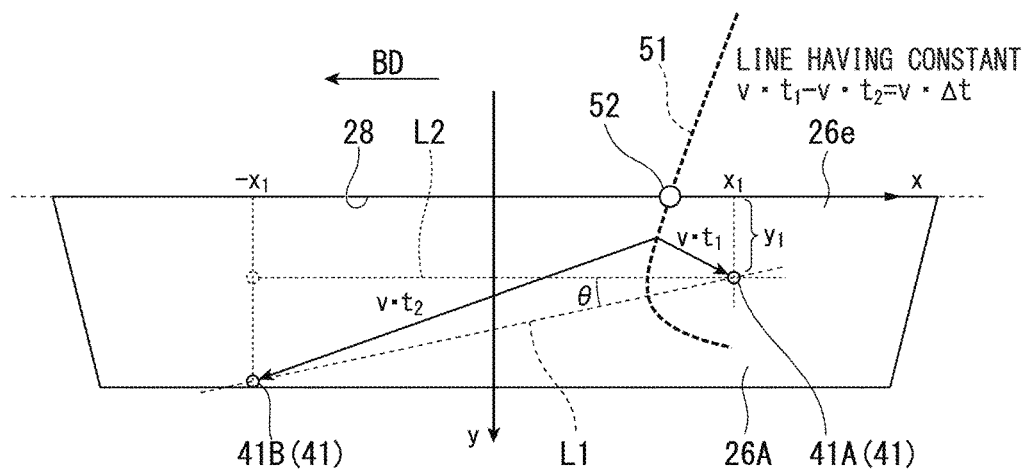
FIG. 8 is a side view conceptually showing a method of orientating a crack position of the embodiment.

The plurality of the AE sensors 41 is disposed so as to be separated from each other in the bridge-axial direction BD. That is, the plurality of the AE sensors 41 is disposed so as to be separated from each other in a direction in which the welded portion 28 extends. Particularly, as shown in FIG. 6B, the plurality of the AE sensors 41 is disposed, for example, at the same height. Particularly, as shown in FIG. 8 described later, the plurality of the AE sensors 41 may be disposed at heights different from each other. In addition, a place to which the AE sensor 41 is attached is not limited to the upright standing portion 26A of the trough rib 23. For example, the AE sensor 41 may be attached to the horizontal portion 27 of the trough rib 23.

In addition, the detection device 2 may include a plurality of AE sensors 43 that detects the crack C of the welded portion 28 provided in the other upright standing portion 26B of the trough rib 23. As shown by a dashed-two dotted line in FIG. 6C, this AE sensor 43 is attached to, for example, the lateral side of the upright standing portion 26B of the trough rib 23.

Next, the second AE sensor group 32 will be described.

As shown in FIGS. 6A to 6C, the second AE sensor group 32 includes a plurality of AE sensors 42. FIGS. 6A to 6C representatively show four AE sensors 42 included in the second AE sensor group 32. Particularly, the second AE sensor group 32 may include, for example, more AE sensors 42 disposed at a predetermined interval in the bridge-axial direction BD.

As shown in FIGS. 6A to 6C, each of the plurality of the AE sensors 42 included in the second AE sensor group 32 is attached to the deck plate 21. Specifically, each AE sensor 42 is attached to the lower surface of the deck plate 21, and is in contact with the deck plate 21. Therefore, each AE sensor 42 detects an elastic wave transmitted from the crack C to the deck plate 21.

The plurality of the AE sensors 42 are disposed so as to be separated from each other in the bridge-axial direction BD, and in a direction (for example, substantially orthogonal to) intersecting the bridge-axial direction BD. That is, some AE sensors 42 included in the second AE sensor group 32 are disposed so as to be separated from each other in a direction in which the welded portion 28 extends. In addition, some AE sensors 42 included in the second AE sensor group 32 are disposed separately on both sides of the trough rib 23 in a direction (for example, substantially orthogonal to) intersecting the bridge-axial direction BD. Hereinafter, the direction (for example, substantially orthogonal to) intersecting the bridge-axial direction BD is simply referred to as a "width direction".

Here, for convenience of description, in the AE sensors 41 and 42 shown in FIGS. 6A to 6C, two AE sensors 41 included in the first AE sensor group 31 are referred to as a first AE sensor 41A and a second AE sensor 41B, respectively. In addition, four AE sensors 42 included in the second AE sensor group 32 are referred to as a third AE sensor 42A, a fourth AE sensor 42B, a fifth AE sensor 42C, and a sixth AE sensor 42D, respectively.

Figure 7:
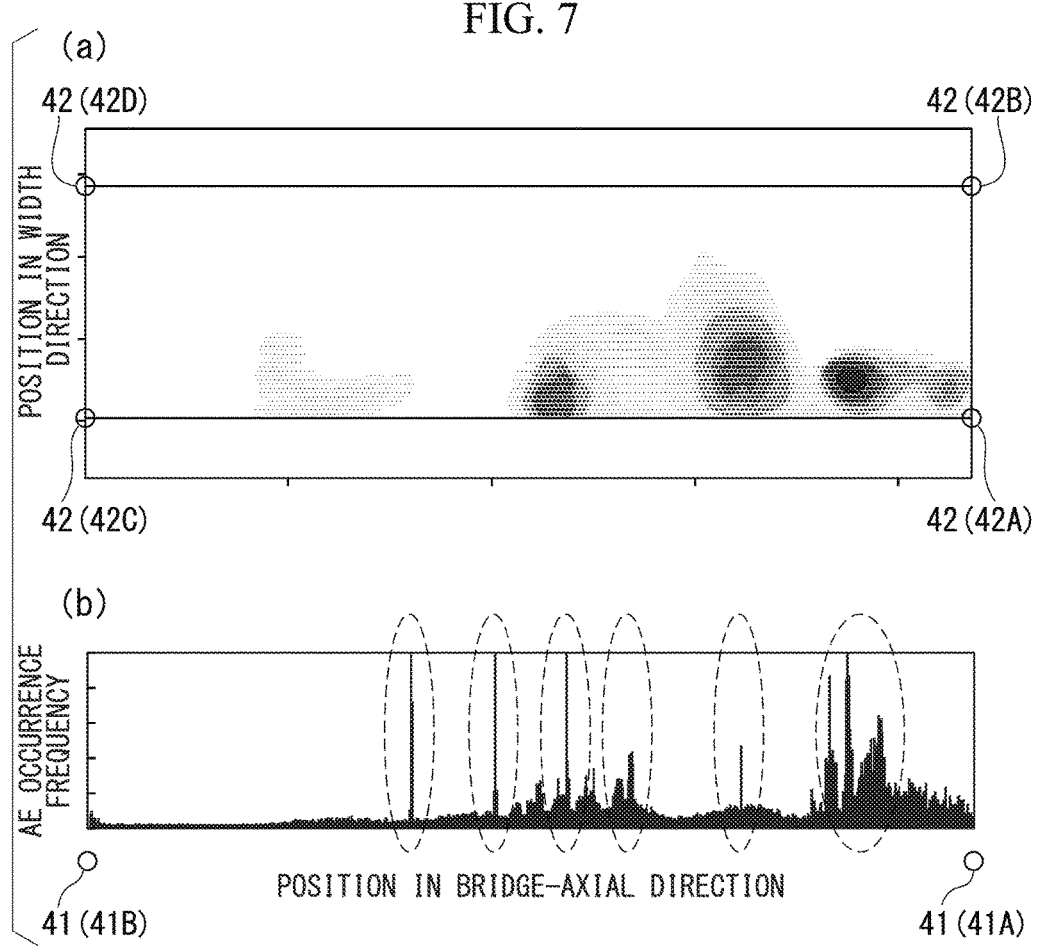
FIG. 7 is a diagram showing an example of detection results of the detection system of the embodiment.

FIG. 7 shows an example of actual detection results of the detection system 1. That is, FIG. 7 is a diagram in which signals detected by the AE sensors 41 and 42 included in the first and second AE sensor groups 31 and 32 in the arrangement example of FIGS. 6A to 6C are analyzed, and the detection results of the AE occurrence frequency are displayed. Particularly, (a) of FIG. 7 shows the detection results of the AE occurrence frequency based on the second AE sensor group 32 (AE sensors 42 attached to the deck plate 21). In (a) of FIG. 7, as a color in the drawing becomes darker, a higher AE occurrence frequency is shown. On the other hand, (b) of FIG. 7 shows the detection results of the AE occurrence frequency based on the first AE sensor group 31 (AE sensors 41 attached to the trough rib 23). In (b) of FIG. 7, as a bar graph in the drawing becomes higher, a higher AE occurrence frequency is shown.

As described above, when the crack C is generated in the welded portion 28, an elastic wave is generated. This elastic wave propagates from the crack C to the deck plate 21 and the trough rib 23. Here, noise may be applied to the bridge structure 10 from the vehicle V traveling along the traveling surface TS. In addition, directions in which the elastic wave propagates more intensively may be different from each other due to a difference in the progress direction of the crack C, the penetration state of welding, or the like.

Here, it has been found by the inventors' research that even an elastic wave which is not capable of being detected in the AE sensors 42 attached to the deck plate 21 can be detected by installing the AE sensors 41 in the trough rib 23. That is, as shown in FIG. 7, it can be understood that even in a plurality of places in which an elastic wave is not detected in the AE sensors 42 attached to the deck plate 21, an elastic wave associated with the crack C can be detected by the AE sensors 41 attached to the trough rib 23. That is, it has been found that the installation of the trough rib 23 in the AE sensor 41 increases the accuracy of detection of the crack C.

Next, a method of orientating a position of the crack C will be described.

In the embodiment, the position of the crack C is orientated using the detection results of two AE sensors 41A and 41B next to each other included in the first AE sensor group 31. Particularly, the term "orientating" referred to in the embodiments means, for example, obtaining (calculating, or specifying) the position or the like of a target based on the detection results of the sensors.

FIG. 8 is a side view conceptually showing a method of orientating a position of the crack C.

As shown in FIG. 8, in the embodiment, the generation source position of an elastic wave (position of the crack C) is orientated based on a time difference between times at which two AE sensors 41A and 41B detect an elastic wave, the propagation velocity of the elastic wave in the trough rib 23, and the position of the welded portion 28.

Specifically, the curve of a broken line shown in FIG. 8 is a hyperbolic curve 51 using two AE sensors 41A and 41B as focuses. That is, in each point located on the line of the hyperbolic curve 51, a difference between distances from the two AE sensors 41A and 41B with respect to the hyperbolic curve 51 is constant. In other words, when the propagation velocity of the elastic wave in the trough rib 23 is set to v, and a time difference ($t_1 - t_2$) between a time ($t_1$) at which the first AE sensor 41A detects the elastic wave and a time ($t_2$) at which the second AE sensor 41B detects the elastic wave is set to $\Delta t$, the hyperbolic curve 51 is a line linking points at which $v \times \Delta t$ become constant. Particularly, the wording "time at which a sensor detects an elastic wave" referred to in the embodiments may be replaced by the wording "time at which an elastic wave reaches a sensor".

Here, the crack C can be presumed to occur in the welded portion 28. In addition, the welded portion 28 is linearly provided along the end 26e of the trough rib 23. Therefore, as shown in FIG. 8, regarding a point of intersection (intersection portion) 52 between the hyperbolic curve 51 and the welded portion 28, only one point is determined. The point of intersection 52 at which the hyperbolic curve 51 and the welded portion 28 intersect each other can be orientated as the generation source position of an elastic wave (position of the crack C). Therefore, even when the AE sensor 41 is provided in a place away from the welded portion 28, the position of the crack C can be accurately orientated.

Here, when the volume elastic modulus of a material is set to $\kappa$ (Pa), and the density thereof is set to $\rho_0$ (kg/m³), the propagation velocity v of an elastic wave propagating through the material can be represented by the following expression.

(Expression 1)

$$v = \sqrt{\frac{\kappa}{\rho_0}} \quad (1)$$

In addition, in the case of a three-dimensional object, when the shear elastic modulus thereof is set to G, the following expression can be represented.

(Expression 2)

$$v = \sqrt{\frac{1}{\rho_0} \cdot \left(\kappa + \frac{4}{3}G\right)} \quad (2)$$

This means that the propagation velocity v of an elastic wave propagating through a material is determined by a physical value intrinsic to the material. Therefore, it is possible to calculate the propagation velocity v of an elastic wave in advance with respect to a material, and to prepare a look-up table. That is, in a case where the propagation velocity v is selected in the calculation of the position orientation of the crack C, it is possible to appropriately select a propagation velocity depending on a material by referring to the look-up table.

Next, a relationship between the position of the AE sensor 41 and the accuracy of detection of the crack C will be described.

Here, the size of the crack C to be detected in the embodiment is, for example, 3 mm at a minimum. Such a numerical value of 3 mm can be obtained from a crack progress limit curve. That is, when a crack shape parameter is set to a [mm], a stress range is set to $\Delta\sigma$ [MPa], a threshold stress intensity factor range is set to $\Delta K_{th}$ [MPa/m$^{0.5}$], a correction factor determined depending on a material is set to F, a relationship between the progress of the crack and stress can be represented by the following crack progress limit curve.

(Expression 3)

$$\Delta K_{th} = F \cdot \Delta\sigma \cdot \sqrt{\pi a} \quad (3)$$

Figure 9:
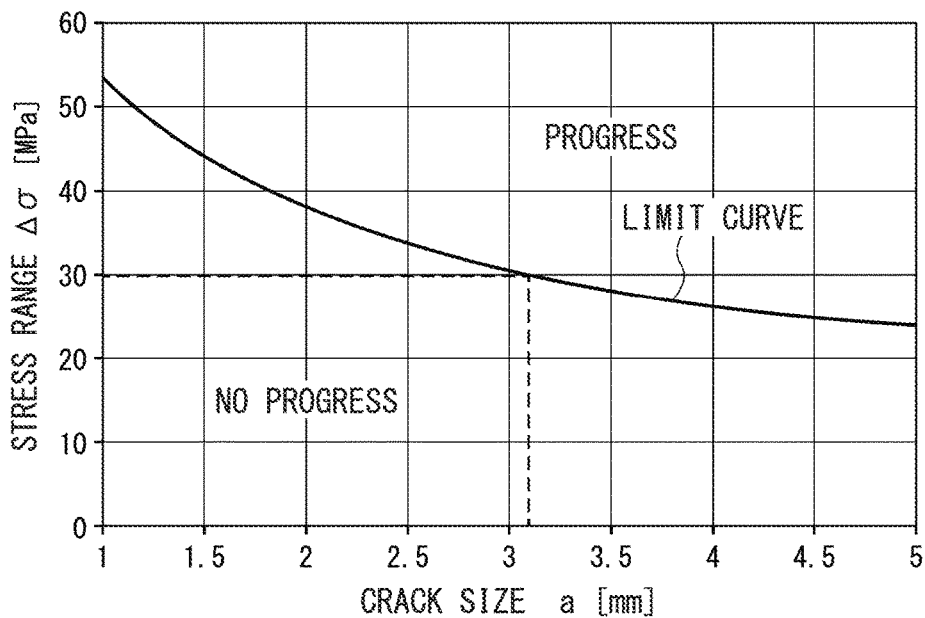
FIG. 9 is a graph showing a crack progress limit curve of the embodiment.

FIG. 9 shows a crack progress limit curve based on Expression (3).

As shown in FIG. 9, when a relationship between the size of the crack C and stress is under the curve, the crack C does not progress. Here, a maximum stress range assumed in the lower surface of the deck plate 21 is 30 MPa. Therefore, the crack C having a size of less than 3 mm can be presumed not to progress. In other words, when the crack C having a size of 3 mm or greater can be detected, it is possible to detect the status of deterioration of the bridge structure 10 with a good degree of accuracy.

Here, a relationship between the size of the crack C and the variation of an orientation position will be described.

Figure 10:
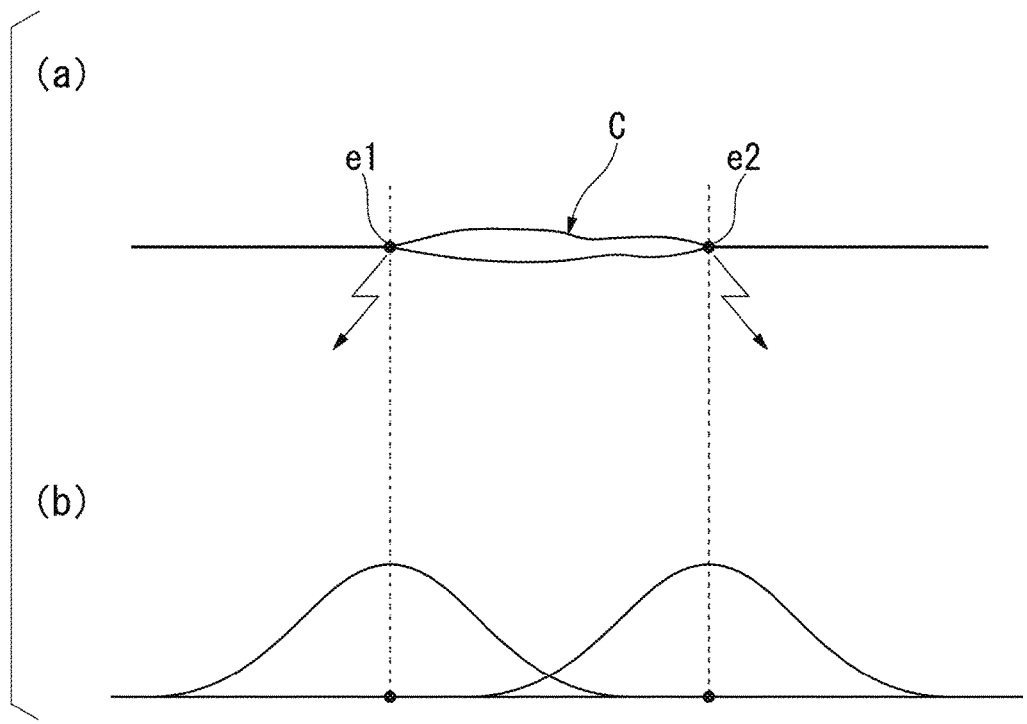
FIG. 10 is a diagram showing a relationship between the size of a crack of the embodiment and the variation of an orientation position.

FIG. 10 shows a relationship between the size of the crack C and the variation of the orientation position (orientation error) of the generation source of an elastic wave. Particularly, (a) of FIG. 10 shows an example of the crack C having a size of 3 mm. In addition, (b) of FIG. 10 shows the distribution of variations of the orientation position of the generation source of an elastic wave.

As shown in (a) of FIG. 10, in a case where the crack C is large to a certain extent, elastic waves generated from the crack C are generated on both ends e1 and e2 of the crack C. Here, assuming that the variation of the orientation position of the generation source of the elastic wave is larger than 3 mm, the orientation position varies in a range including both ends e1 and e2 of the crack C, and thus it may be difficult to make a determination of the crack C having a size of 3 mm or greater, or the crack C having a size of less than 3 mm. On the other hand, in a case where the variation of the orientation position of the generation source of the elastic wave is smaller than 3 mm, it is possible to distinctively detect an elastic wave emitted from one end e1 of the crack C and an elastic wave emitted from the other end e2 of the crack C. Therefore, in a case where the variation of the orientation position of the generation source of the elastic wave is smaller than 3 mm, it is possible to more reliably find the crack C having a size of 3 mm or greater.

Next, the position of the AE sensor 41 for making the variation of the orientation position of the generation source of the elastic wave smaller than 3 mm will be described.

Here, referring back to FIG. 8, an extension line L1, a reference line L2, and a setting parameter θ are defined.

The extension line L1 is a line extending a straight line passing through two AE sensors 41A and 41B next to each other. The reference line L2 is a line along a direction in which the welded portion 28 extends. For example, the reference line L2 is a line that passes through the first AE sensor 41A, and is substantially parallel to the welded portion 28 (substantially parallel to the traveling surface TS). The setting parameter θ is an angle between the extension line L1 and the reference line L2. Here, the inventors have found that the variation of the orientation position of the generation source of the elastic wave changes due to a difference in the installation parameter θ.

Figure 11A:
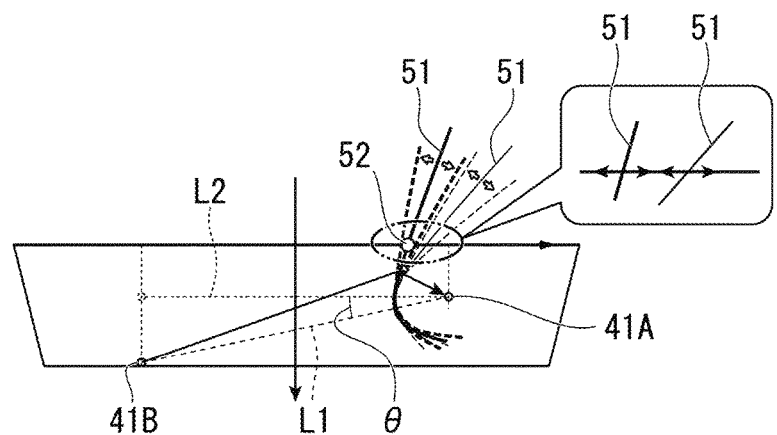
FIGS. 11A and 11B are diagrams showing a relationship between an installation parameter θ of the embodiment and the variation of the orientation position.
Figure 11B:
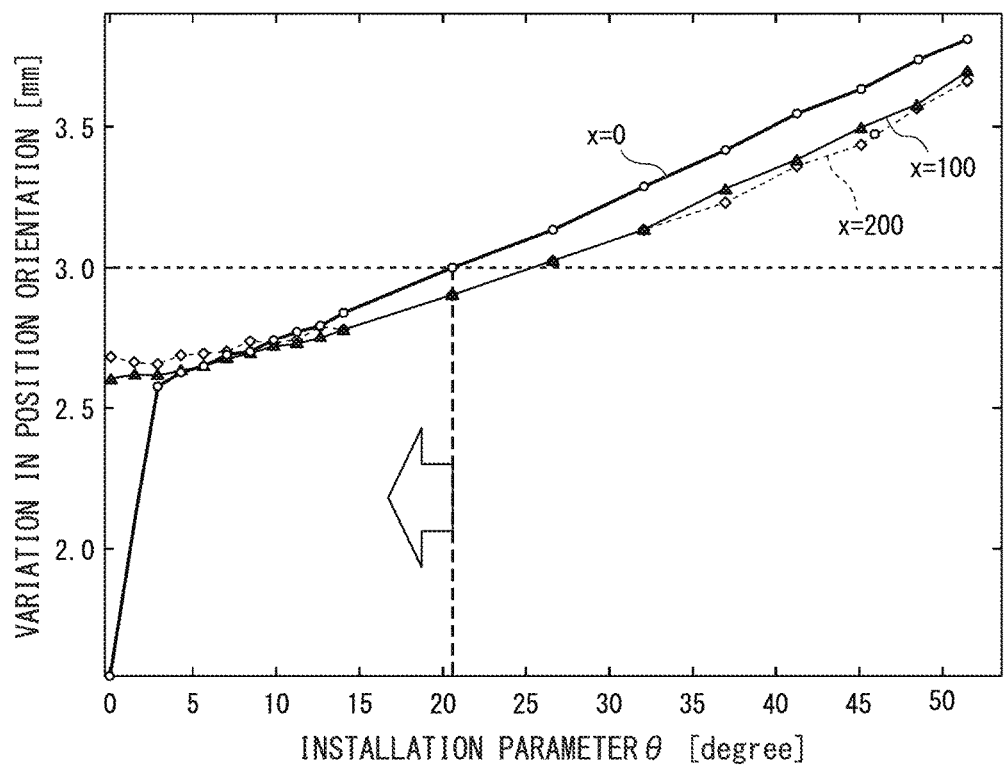

FIGS. 11A and 11B show a relationship between the installation parameter θ and the variation of the orientation position. Particularly, FIG. 11A conceptually shows a change in the variation of the orientation position due to a change in the installation parameter θ. FIG. 11B shows the simulation results of a change in the variation of the orientation position in a case where the installation parameter θ is changed.

As shown in FIG. 11A, a change in the installation parameter θ leads to a change in the intersection angle of the hyperbolic curve 51 with respect to the welded portion 28. Therefore, a change in the installation parameter θ leads to a change in the variation of the orientation position of the generation source position of the elastic wave.

FIG. 11B shows results obtained by performing a Monte Carlo simulation based on the arrangement example of FIGS. 6A to 6C, and calculating the variation of the orientation position of the generation source of the elastic wave with respect to the installation parameter θ. Particularly, in the simulation conditions, $x_1$ is set to 400 mm, $y_1$ is set to 100 mm, and the number of trials is set to 34,000. In addition, the generation source position of the elastic wave is calculated with respect to three kinds of x=0, x=100, and x=200.

As shown in FIG. 11B, it has been found that, as a result of the simulation, the variation of the orientation position of the generation source of the elastic wave becomes smaller than 3 mm in a case where the installation parameter θ is smaller than 20 degrees, regardless of the generation source position of the elastic wave. That is, in a case where two AE sensors 41A and 41B are disposed so as to satisfy a relation of −20 degrees<θ<20 degrees, the variation of the orientation position of the generation source of the elastic wave can be made to be smaller than 3 mm.

In summary, in a case where the two AE sensors 41A and 41B are disposed so as to satisfy a relation of −20 degrees<θ<20 degrees, the variation of the orientation position of the generation source of the elastic wave can be made to be smaller than 3 mm. In a case where the variation of the orientation position of the generation source of the elastic wave can be made to be smaller than 3 mm, it is possible to more reliably detect the crack C having a size of 3 mm or greater. In a case where the crack C having a size of 3 mm or greater can be more reliably detected, it is possible to more accurately detect the status of deterioration of the bridge structure 10.

Next, referring back to FIG. 5, the BPF 33, the ADC 34, the signal processor 35, and the wireless transmitter 36 of the detection device 2 will be described.

The bandpass filter (BPF) 33 is provided between the first and second AE sensor groups 31 and 32 and the ADC 34. Voltage signals which are output from the AE sensors 41 and 42 of the first and second AE sensor groups 31 and 32 are input to the BPF 33, and noise components except for a signal band are removed.

The analog-digital converter (ADC) 34 is provided between the BPF 33 and the signal processor 35. A signal having passed through the BPF 33 is input to the ADC 34. The signal which is input to the ADC 34 is input to the signal processor 35 as discretized waveform data.

The signal processor (signal processing circuit) 35 is formed by, for example, a field programmable gate array (FPGA). For example, in a case where the signal processor 35 is formed by a non-volatile FPGA, it is possible to suppress power consumption during standby. Particularly, the signal processor 35 may be formed by an exclusive LSI.

Figure 12:
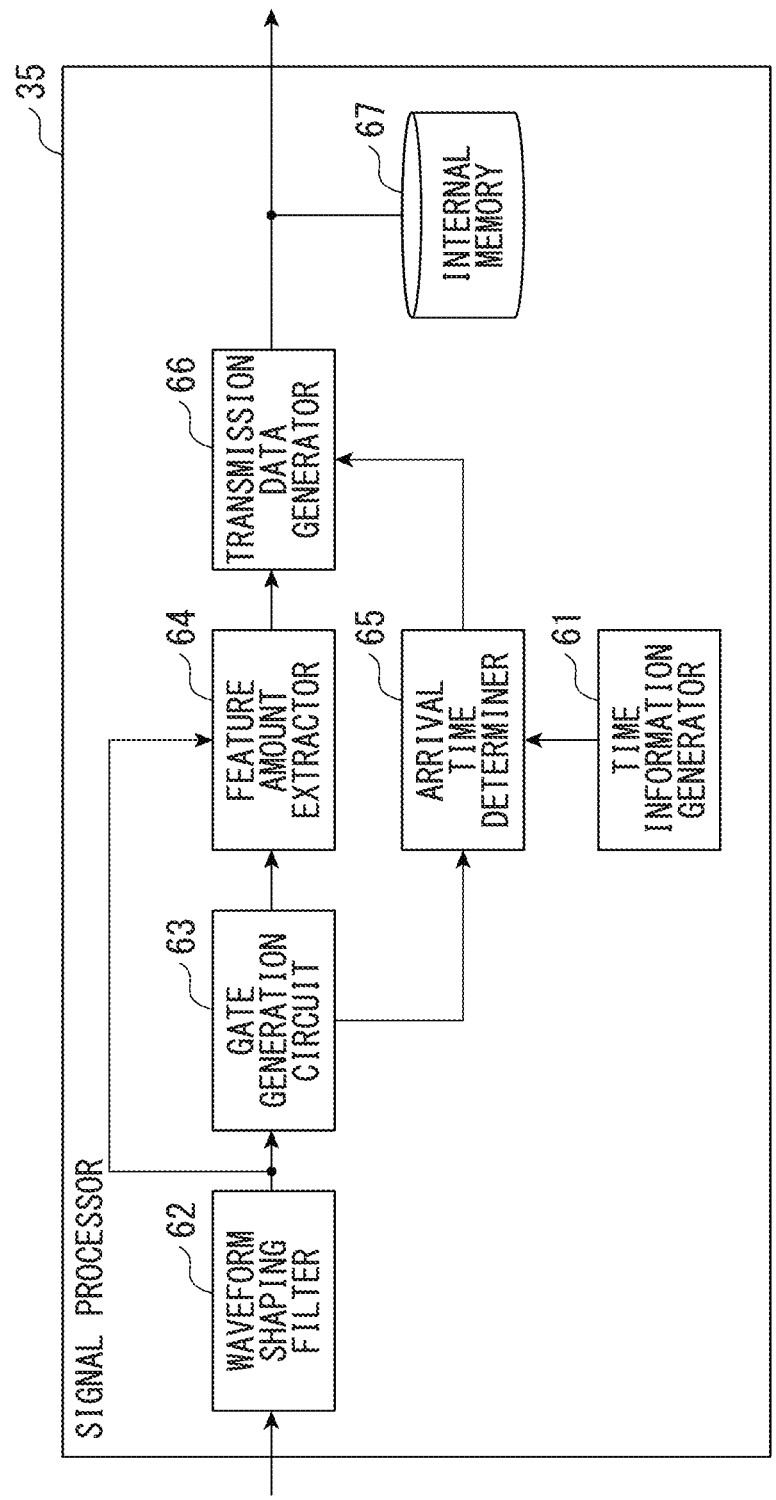
FIG. 12 is a block diagram showing a system configuration of a signal processor of the embodiment.

FIG. 12 is a block diagram showing a system configuration of the signal processor 35.

As shown in FIG. 12, the signal processor 35 includes a time information generator 61, a waveform shaping filter 62, a gate generation circuit 63, a feature amount extractor 64, an arrival time determiner 65, a transmission data generator 66, and an internal memory 67.

The time information generator 61 generates time information of accumulation from the time of power-on of the detection device 2, based on a signal from a clock source such as a crystal oscillator. For example, the time information generator 61 includes a counter that counts the edge of a clock, and sets the value of a register of the counter to time information.

Specifically, the register of the counter has a predetermined bit length b. When a time resolution is set to dt, and a continuous measurement time is set to y, the predetermined bit length b is an integer for satisfying the following relation. (Expression 4)

$$2^b \geq y/dt \qquad (4)$$

That is, the bit length b is determined from the time resolution dt and the continuous measurement time y.

In addition, when the propagation velocity of the elastic wave based on the material of the bridge structure 10 (for example, material of the trough rib 23) is set to v, and position orientation accuracy is set to dr, the time resolution dt is obtained from the following relation. (Expression 5)

$$dt = dr/v \qquad (5)$$

That is, the time resolution dt is determined from the propagation velocity v of the elastic wave and the position orientation accuracy dr. In other words, by determining the bit length b based on the position orientation accuracy dr, it is possible to set the position orientation accuracy dr to an optional range, and to realize a necessary and sufficient position orientation.

For example, in a case where a structure which is a target is assumed to be made of iron, the relation of the propagation velocity v of the elastic wave=5,950 [m/s] is established. When the position orientation accuracy of the generation source of the elastic wave is set to 3 mm, and the number of years of continuous measurement is set to 100, the relation of dt=0.50 [μsec] is established.

Therefore, the relation of b≥53 bits is established.

Here, regarding the transmission packet of a general wireless module, data transmission is performed in units of bytes. Therefore, the bit length b is set to a multiple of 8 for satisfying Expression (4). That is, the relation of the bit length b≥56 bits=7 bytes is established, and thus it is possible to use a general-purpose wireless module.

The waveform shaping filter 62 is provided between the ADC 34 and the gate generation circuit 63. A signal (waveform data) which is input from the ADC 34 to the signal processor 35 is passed through the waveform shaping filter 62. The signal having passed through the waveform shaping filter 62 is input to the gate generation circuit 63 and the feature amount extractor 64.

The gate generation circuit 63 extracts a series of continuous waveforms. The gate generation circuit 63 includes, for example, an envelope detector and a comparator. For example, in a case where the detected envelope is equal to or greater than a predetermined threshold, the gate generation circuit 63 outputs a gate signal which is set to be high (H).

On the other hand, in a case where the detected envelope falls below the threshold, the gate generation circuit 63 outputs to a gate signal which is set to be low (L).

The feature amount extractor 64 is an example of an "extractor". In a case where the gate signal which is output from the gate generation circuit 63 is set to be H, the feature amount extractor 64 processes waveform data, and extracts the feature amount of the waveform shape of the elastic wave (parameter featuring the waveform shape). The feature amount of the waveform shape is an example of "information relating to the characteristics of the elastic wave". In each elastic wave, the feature amount extractor 64 extracts, for example, at least one value of the amplitude of a signal, energy, a rising time, a time duration, a frequency, a zero cross count number and the like, as the feature amount of the waveform shape. Particularly, "information relating to certain contents (for example, characteristics of the elastic wave)" referred to in the embodiments may be information include the contents directly, or may be information in which the contents can be extracted by arithmetic processing, determination processing or the like which is set in advance being performed.

Figure 13:
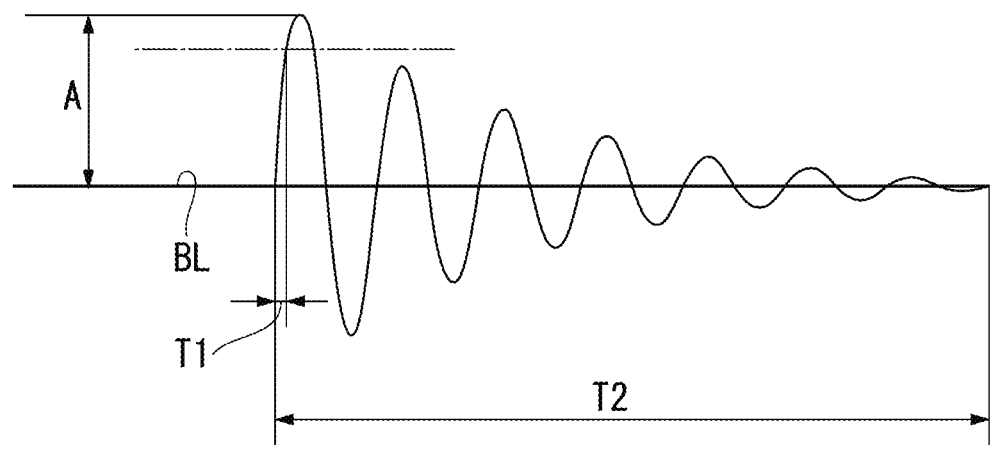
FIG. 13 is a diagram showing parameters relating to the characteristics of an elastic wave of the embodiment.

FIG. 13 shows a specific example of parameters relating to the characteristics of the elastic wave.

As shown in FIG. 13, the term "amplitude of a signal" refers to, for example, a value of a maximum amplitude A in the elastic wave. The term "energy" refers to, for example, a value obtained by performing time integration on a value obtained by rasing an amplitude to the second power at each point in time. Particularly, the definition of the "energy" is not limited to the above example, and may be approximated using, for example, the envelope of a waveform. The term "rising time" refers to, for example, a time T1 which is taken until the elastic wave rises in excess of a predetermined value which is set in advance from a zero value. The term "time duration" refers to, for example, a time T2 which is taken until the amplitude becomes smaller than a value which is set in advance from the rising start of the elastic wave. The term "frequency" refers to a frequency of the elastic wave. The term "zero cross count number" refers to, for example, the number of times by which the elastic wave traverses the reference line BL passing through a zero value.

The feature amount extractor 64 extracts the feature amount of the waveform shape of the elastic wave in each of the AE sensors 41 and 42, based on the detection result of each of the AE sensors 41 and 42. The feature amount extractor 64 sends information relating to the extracted feature amount of the waveform shape in each of the AE sensors 41 and 42 to the transmission data generator 66.

On the other hand, as shown in FIG. 12, the arrival time determiner 65 receives time information from the time information generator 61. In addition, the arrival time determiner 65 receives a gate signal indicating the presence or absence of an AE signal from the gate generation circuit 63. The arrival time determiner 65 generates arrival time information of the elastic wave based on the time information received from the time information generator 61 and the gate signal received from the gate generation circuit 63. For example, the arrival time determiner 65 sets the time information when the rising edge of the gate signal is generated, to the arrival time of the elastic wave.

The arrival time determiner 65 calculates the arrival time of the elastic wave with respect to each of the AE sensors 41 and 42, based on the detection result of each of the AE sensors 41 and 42. The arrival time determiner 65 sends information relating to the calculated arrival time of the elastic wave with respect to each of the AE sensors 41 and 42, to the transmission data generator 66.

The transmission data generator 66 associates information relating to the feature amount of the waveform shape, received from the feature amount extractor 64, in each of the AE sensors 41 and 42, and information relating to the arrival time of the elastic wave, received from the arrival time determiner 65, in each of the AE sensors 41 and 42, and generates AE data of one group for transmission. The generated AE data is saved in the internal memory 67. The internal memory 67 is, for example, a dual port RAM. Particularly, the generated AE data may be sent directly to the wireless transmitter 36 (see FIG. 5) without being saved in the internal memory 67.

Next, the wireless transmitter 36 will be described with reference to FIG. 5.

The wireless transmitter (wireless transmitting circuit) 36 includes, for example, an antenna and a wireless module that generates a high-frequency signal. The wireless transmitter 36 wirelessly transmits AE data at a predetermined timing which is set in advance. The wireless transmitter 36 is an example of each of the "outputter" and the "transmitter". The wireless transmitter 36 outputs information obtained from outputs of the AE sensors 41 and 42 to the outside. Particularly, the "information obtained from the output of the AE sensors" may be the voltage signal itself which is output from the AE sensor, or may be obtained by performing noise processing, arithmetic processing, determination processing or the like, which is set in advance, on the voltage signal. In addition, in a case where a deterioration detector 72 described later is provided within the detection device 2, the "information obtained from an output of the AE sensor" which is output by the wireless transmitter 36 may include information relating to the presence or absence of the deterioration of the bridge structure 10 or the degree of deterioration thereof.

In the embodiment, the wireless transmitter 36 transmits information relating to the feature amount of the waveform shape of the elastic wave in each of the AE sensors 41 and 42 and information relating to the arrival time of the elastic wave in each of the AE sensors 41 and 42, as information obtained from outputs of the AE sensors 41 and 42, in association therewith.

Next, the information collection device 3 and the information processing device 4 will be described.

As shown in FIG. 5, the information collection device 3 includes a wireless receiver (wireless receiving circuit) 71. The wireless receiver 71 includes, for example, an antenna and a wireless module that processes a high-frequency signal.

One information collection device 3, for example, is provided in one bridge structure 10. In addition, the wireless receiver 71 includes a storage DB which is not shown. The wireless receiver 71 receives the AE data from one or more detection devices 2 provided in the bridge structure 10, and saves the received AE data in the storage DB.

The information processing device 4 is, for example, an electronic device (for example, server) which is provided in the management office of an organization that manages the bridge structure 10. The information processing device 4 includes the deterioration detector 72. All or some of respective function portions of the deterioration detector 72 are realized by, for example, a program being executed by the processor (for example, central processing unit (CPU)) of the information processing device 4. Instead of this, all or some of the respective function portions of the deterioration detector 72 may be formed by hardware (for example, large scale integration (LSI)) included in the information processing device 4.

Figure 14:
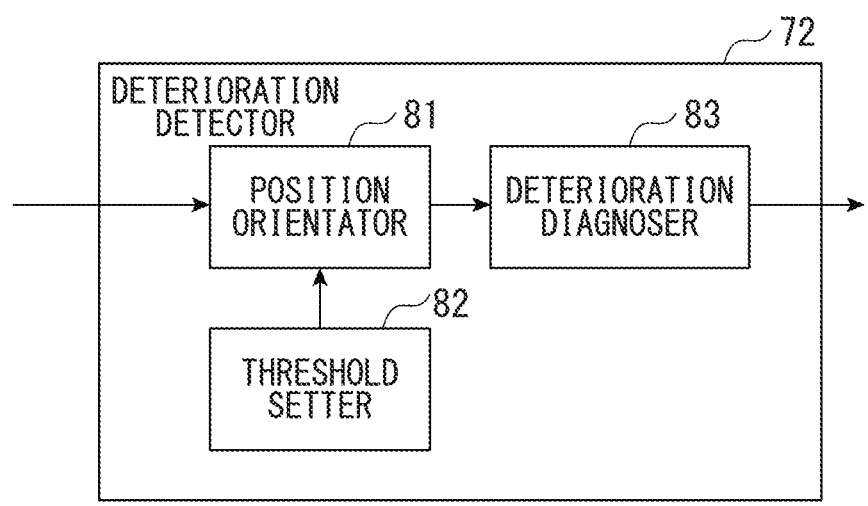
FIG. 14 is a block diagram showing a system configuration of a deterioration detector of the embodiment.

FIG. 14 is a block diagram showing a system configuration of the deterioration detector 72.

As shown in FIG. 14, the deterioration detector 72 includes a position orientator 81, a threshold setter 82, and a deterioration diagnoser 83.

The position orientator 81 is an example of the "orientator", and orientates the generation source position of the elastic wave. Specifically, the position orientator 81 reads an AE data group within the storage DB of the wireless receiver 71 at a predetermined timing which is set in advance. The position orientator 81 compares pieces of information relating to the feature amount of the waveform shape of the elastic wave in each of the AE sensors 41 and 42, to thereby determine whether the elastic waves detected by the respective AE sensors 41 and 42 are the same as each other. That is, the position orientator 81 compares at least one (for example, two or more) of the amplitude, energy, rising time, time duration, frequency, zero cross count number and the like of a signal of the elastic wave detected by each of the AE sensors 41 and 42 (for example, AE sensors 41A and 41B), to thereby determine whether the elastic waves detected by the respective AE sensors 41 and 42 (for example, AE sensors 41A and 41B) are the same as each other.

In a case where the similarity of the feature amount of the waveform shape (similarity of the waveform shape) of the elastic wave in a plurality of AE sensors 41 (or a plurality of AE sensors 42) is in a predetermined range which is set in advance, the position orientator 81 determines that the elastic waves detected by the plurality of the AE sensors 41 (or the plurality of the AE sensors 42) are the same elastic wave, and orientates the generation source position of the elastic wave. Particularly, the determination of the similarity of the elastic wave is separately performed in the AE sensor 41 attached to the trough rib 23 and the AE sensor 42 attached to the deck plate 21. This is because the plate thickness of the trough rib 23 and the plate thickness of the deck plate 21 are different from each other, and because the waveform shape of the elastic wave input to the AE sensor 41 and the waveform shape input to the AE sensor 42 are different from each other.

Specifically, as described above with reference to FIG. 8, the position orientator 81 orientates the generation source position of an elastic wave, based on a time difference between times at which two AE sensors 41A and 41B detect an elastic wave, the propagation velocity of the elastic wave in the trough rib 23, and the position of the welded portion 28. That is, the position orientator 81 orientates a point of intersection 52 between the hyperbolic curve 51 and the welded portion 28 in FIG. 8, as the generation source position of the elastic wave.

In addition, the position orientator 81 performs noise processing associated with the position orientation. The position orientator 81 is an example of a noise removal portion which removes noise, based on a predetermined algorithm which is set in advance.

For example, the position orientator 81 receives a threshold serving as a determination criterion of noise processing from the threshold setter 82. The threshold stored in the threshold setter 82 can be changed by a user. The position orientator 81 presumes the elastic wave which is determined to occur from the outside of a range of a predetermined threshold, as a noise, based on a position orientation result. In this manner, in noise removal, it is determined whether the elastic wave is a noise or a significant signal, based on a predetermined threshold. Therefore, it is possible to flexibly change threshold conditions by noise processing being performed on the server side. That is, it is possible to add many conditions such as conditions of an installation status and a measurement target, climate conditions, and flexibly set thresholds. Therefore, it is possible to more effectively remove noise.

The deterioration diagnoser 83 determines the status of deterioration of the bridge structure 10, based on information subjected to the noise processing in the position orientator 81. The deterioration diagnoser 83 is an example of a "determiner". The deterioration diagnoser 83 detects the presence or absence of deterioration or the degree of deterioration of the bridge structure 10, based on information relating to the generation source position of the elastic wave. For example, the deterioration diagnoser 83 determines the presence or absence of deterioration or the degree of deterioration of the bridge structure 10, based on information relating to the density of the generation source position of the elastic wave which is obtained by accumulating information on the generation source position of the elastic wave which is oriented by the position orientator 81. For example, in a case where the space density of the generation source of the elastic wave exceeds a predetermined value which is set in advance, the deterioration diagnoser 83 determines that there is deterioration (or the degree of deterioration of a certain level). Particularly, the deterioration diagnoser 83 is not limited to the above example. For example, the deterioration diagnoser 83 may determine the presence or absence of deterioration or the degree of deterioration of the bridge structure 10, based on the occurrence frequency of the elastic wave or the intensity of the elastic wave (for example, amplitude or energy).

Next, a description will be given on a detection method using the detection system 1 according to the embodiment (a deterioration detection method or a deterioration diagnosis method).

Figure 15:
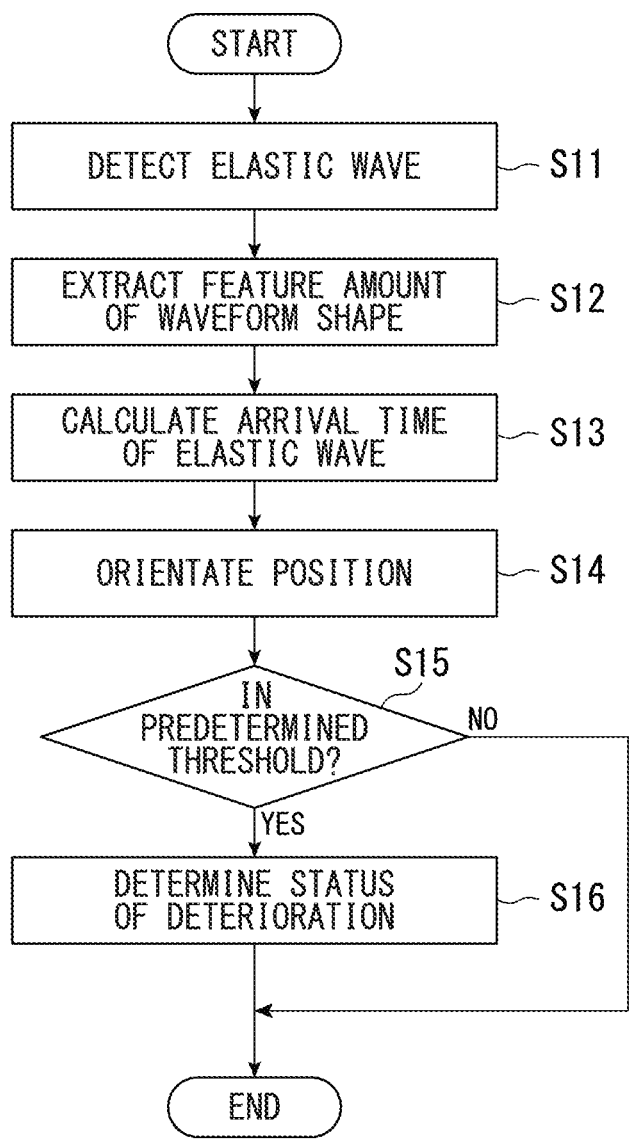
FIG. 15 is a flow diagram showing an example of a flow of a detection method of the embodiment.

FIG. 15 is a flowchart showing an example of a flow of the detection method of the embodiment.

As shown in FIG. 15, first, an elastic wave associated with the generation of the crack C or the progress of the crack C is detected by using the AE sensors 41 and 42 provided in the bridge structure 10 (step S11). In the embodiment, for example, an elastic wave transmitted from the crack C to the trough rib 23 is detected by the AE sensor 41 attached to the trough rib 23.

Next, the feature amount featuring the waveform shape of the elastic wave detected by each of the AE sensors 41 and 42 (a parameter featuring a waveform shape) is extracted, based on the detection result by each of the AE sensors 41 and 42 (step S12). In addition, the arrival time of the elastic wave for each of the AE sensors 41 and 42 is calculated, based on the detection result by each of the AE sensors 41 and 42 (step S13). Particularly, the step S12 and the step S13 may be performed in a reverse order, or simultaneously performed.

Next, the position orientation of the generation source of the elastic wave is performed (step S14). Specifically, the similarity between the elastic waves detected by, for example, the AE sensors 41A and 41B is calculated based on information relating to the feature amounts of the waveform shapes of the elastic waves. In a case where the similarity between elastic waves detected by the AE sensors 41A and 41B is within a predetermined range, the elastic waves are determined as the same elastic wave, and the position orientation of the generation source of the elastic wave is performed. For example, the position orientation of the generation source of the elastic wave is performed, based on a time difference between times when two AE sensors 41A and 41B detect the elastic waves, the propagation velocity of the elastic wave in the trough rib 23, and the position of the welded portion 28.

Next, a noise processing associated with the position orientation is performed (step S15). Specifically, whether or not the elastic wave is generated within a range of a predetermined threshold is determined based on the position orientation result. In a case where it is determined that the elastic wave is generated within the range of a predetermined threshold (step S15: YES), the process proceeds to a determination of a status of deterioration. On the other hand, in a case where it is determined that the elastic wave is generated out of the range of a predetermined threshold (step S15: NO), signals detected by the AE sensors 41A and 41B are presumed to be noise, and the determination of the degree of deterioration is not performed.

Next, the status of deterioration of the bridge structure 10 is determined (step S16). For example, the status of deterioration is determined based on information relating to the density of the generation source position of the elastic wave. Therefore, the presence or absence of deterioration of the bridge structure 10 or the degree of deterioration is detected.

Particularly, the details of the operations of the respective steps are described in the explanation of the detection system 1.

According to such a configuration, it is possible to provide the detection system 1, the detection device 2, and the detection method, which are capable of simply detecting the crack C occurring in the structure.

That is, for example, a fatigue crack may occur in a welded portion of the deck plate and the trough rib, in the steel plate deck. If the fatigue crack occurs in the welded portion, there is the possibility of the falling of a road or the like being caused.

Therefore, the detection of the fatigue crack is important for the maintenance of the infrastructure.

Here, as a comparative example 1, a detection method of detecting the crack occurring in the structure by an ultrasonic flaw detection method is considered. In such a detection method, since it is necessary to actually bring a probe into contact with the surface of the structure and perform scanning, a worker needs to come close to the structure. Therefore, it is necessary to set up scaffolding for a structure such as a bridge. Therefore, it may be difficult to investigate all over a wide range of the structure.

In addition, as a comparative example 2, a detection method is considered which indirectly detects a crack, by detecting stagnant water which infiltrates into a crack and stagnates in the inside of the structure, with infrared rays. In such a detection method, since the stagnant water is directly detected, if rainwater or the like is not infiltrated from a crack, the crack may not be detected in some cases.

On the other hand, the detection device 2 according to the embodiment is a detection device which is provided in the bridge structure 10 including a deck plate 21 that support from below the traveling surface TS along which the vehicle V travels, a trough rib 23 which is provided on the opposite side of the traveling surface TS, with respect to the deck plate 21, and a welded portion 28 which is provided along an ending portion 26e of the trough rib 23 facing the deck plate 21, and fixes the deck plate 21 and the trough rib 23, includes a plurality of AE sensors 41 and a wireless transmitter 36. The plurality of the AE sensors 41 is disposed so as to be separated from each other in a direction in which the welded portion 28 extends, and are respectively attached to the trough rib 23 so as to detect the elastic wave transmitted to the trough rib 23. The wireless transmitter 36 outputs information obtained from the outputs of the plurality of the AE sensors 41 to the outside.

According to such a configuration, since the elastic wave transmitted from the crack C to the trough rib 23 is detected by the AE sensor 41, it is possible to detect the crack C, for example, even a crack which is difficult to visually view. Furthermore, according to the above configuration, it is possible to detect the crack C, without being restricted to the installation height or state (such as the presence of stagnant water) of the structure.

Here, in the embodiment, a plurality of AE sensors 41 are attached to the trough rib 23 rather than the deck plate 21. In addition, it is possible to detect the crack C which cannot detected by the AE sensor 42 attached to the deck plate 21, by attaching the AE sensor 41 to the trough rib 23 as described above with reference to FIG. 7. Thus, since the AE sensor 41 is attached to the trough rib 23, it is possible to detect the crack C with a good degree of accuracy.

Particularly, one of the reasons that it is possible to detect the crack C which cannot detected by the AE sensor 42 attached to the deck plate 21, by attaching the AE sensor 41 to the trough rib 23, is considered as follows. That is, the deck plate 21 is relatively close to the traveling surface TS along which the vehicle V travels. Therefore, various vibrations are likely to be input from the traveling surface TS to the deck plate 21. In addition, since the AE sensors 41 and 42 are generally high-sensitive, a vibration which is input from the traveling surface TS has a tendency to be detected. For this reason, a signal obtained by detecting the elastic wave and a signal obtained by the vibration which is input from the traveling surface TS are mixed in a signal which is output from the AE sensor 42.

As a result, in a noise removal process, there is a possibility that the signal obtained by detecting the elastic wave is removed along with a noise.

On the other hand, the trough rib 23 is disposed away from the traveling surface TS as compared to the deck plate 21. Therefore, the vibration which is input from the traveling surface TS to the trough rib 23 is limited.

As a result, if the AE sensor 41 is attached to the trough rib 23, it is considered that the crack C can be detected with a good degree of accuracy.

In addition, in the embodiment, the trough rib 23 includes an upright standing portion 26A in a direction away from the traveling surface TS. A plurality of AE sensors 41 is attached to the upright standing portion 26A of the trough rib 23, and detects an elastic wave transmitted to the upright standing portion 26A.

According to such a configuration, the AE sensor 41 is disposed away from the traveling surface TS, as compared to the end 26e of the trough rib 23, in the trough rib 23. Therefore, a noise input from the traveling surface TS to the AE sensor 41 is further reduced. As a result, the accuracy of detection of the crack C can be further enhanced.

In the embodiment, if an angle between a linear extension line L1 linking two AE sensors 41A and 41B next to each other included in a plurality of AE sensors 41 and a reference line L2 in a direction in which the welded portion 28 extends is referred to as θ, the relation of −20 degrees<θ<20 degrees is satisfied.

Here, the trough rib 23 of the bridge structure 10 may have partially holes, protrusions or the like in some cases. In addition, another sensor may be attached to the trough rib 23 in some cases. Therefore, a plurality of AE sensors 41A and 41B may not be disposed at the same height in some cases.

However, it is possible to orientate the crack C with a good degree of accuracy by disposing a plurality of AE sensors 41A and 41B to satisfy the above relationship. Therefore, it is possible to detect the status of deterioration of the bridge structure 10 with a good degree of accuracy detect.

In the embodiment, a plurality of AE sensors 42 are further included which are disposed so as to be separated from each other in a direction in which the welded portion 28 extends, and are respectively attached to the deck plate 21 so as to detect the elastic wave transmitted to the deck plate 21. The wireless transmitter 36 outputs information obtained from the outputs of a plurality of AE sensors 41 attached to the trough rib 23 and a plurality of AE sensors 42 attached to the deck plate 21 to the outside.

According to such a configuration, since the plurality of the AE sensors 42 attached to the deck plate 21 in addition to the plurality of the AE sensors 41 attached to the trough rib 23 are concurrently used, the accuracy of detection of the crack C can be further enhanced. In addition, as shown in FIG. 6A, since the plurality of the AE sensors 42 are separately disposed in both sides of the trough rib 23 in the width direction of the bridge structure 10, it is possible to detect the position of the crack C in a two-dimensional plane.

In the embodiment, the detection device 2 further includes a feature amount extractor 64. The feature amount extractor 64 extracts information relating to the characteristics of the elastic waves of the AE sensors 41A and 41B, for example, based on the detections results of the AE sensors 41A and 41B. The wireless transmitter 36 outputs the information relating to the characteristics of the elastic waves of the AE sensors 41A and 41B which is extracted by the feature amount extractor 64 and the information relating to the arrival times of the elastic waves for the AE sensors 41A and 41B in association with each other.

According to such a configuration, it is possible to determine whether or not the elastic waves detected by the AE sensors 41A and 41B are the same elastic wave, based on the information relating to the characteristics of the elastic waves, with a high level of accuracy.

Therefore, the accuracy of detection of the crack C can be further enhanced.

The detection system 1 according to the embodiment is a detection system which detects the state of the bridge structure 10, and includes a plurality of AE sensors 41, and a position orientator 81. The position orientator 81 orientates the generation source position of the elastic wave, based on the information obtained from the outputs of the plurality of the AE sensors 41.

According to such a configuration, as described above, since the elastic wave transmitted from the crack C to the trough rib 23 is detected by the AE sensor 41, it is possible to detect the crack C, for example, even a crack which is difficult to visually view, without being restricted to the installation height or state of the structure.

In the embodiment, a plurality of AE sensors 41 includes a first AE sensor 41A, and a second AE sensor 41B. The position orientator 81 orientates the generation source position of the elastic wave, based on a time difference between arrival times of the elastic waves for the first AE sensor 41A and the second AE sensor 41B, the propagation velocity of the elastic wave in the trough rib 23, and the position of the welded portion 28.

According to such a configuration, it is possible to detect the position of the crack C with a good degree of accuracy, even by the AE sensors 41A and 41B disposed away from the position of the actual crack C.

In the embodiment, in a case where the similarity between the characteristics of the elastic wave of the first AE sensor 41A and the characteristics of the elastic wave of the second AE sensor 41B is within a range which is set in advance, the position orientator 81 determines that the elastic wave detected by the first AE sensor 41A and the elastic wave detected by the second AE sensor 41B are the same elastic wave, and orientates the generation source position of the elastic wave.

According to such a configuration, it is possible to determine whether or not the elastic wave detected by the first AE sensor 41A and the elastic wave detected by the second AE sensor 41B are the same elastic wave with a good degree of accuracy. Therefore, the accuracy of detection of the crack C can be further enhanced.

In the embodiment, the detection system 1 further includes a deterioration diagnoser 83. For example, the deterioration diagnoser 83 determines the deterioration status of the bridge structure 10, based on information relating to the density of the generation source position of the elastic wave which is obtained by accumulating information on the generation source position of the elastic wave which is oriented by the position orientator 81. Furthermore, "determination of a deterioration status" referred to in the embodiments includes determination of at least any of the presence or absence of deterioration and the degree of deterioration.

According to such a configuration, it is possible to detect the deterioration status of the bridge structure 10, based on the density of the generation source position of the elastic wave, easily and with a relatively high level of accuracy.

The detection method according to the embodiment is a detection method of detecting the status of the bridge structure 10, and orientates the generation source position of the elastic wave, based on a detection result obtained by detecting the elastic wave transmitted to the trough rib 23 at a plurality of positions separated from each other in a direction in which the welded portion 28 extends. Furthermore, "detection result" referred to in the embodiments may be a voltage signal which is output from the AE sensor, or a signal obtained by performing noise processing, arithmetic processing, determination processing, or the like, which is set in advance, on the voltage signal.

According to such a configuration, as described above, since the elastic wave transmitted from the crack C to the trough rib 23 is detected by the AE sensor 41, it is possible to detect the crack C, for example, even a crack which is difficult to visually view, without being restricted to the installation height or state of the structure.

Hitherto, the detection system 1, the detection device 2, and the detection method according to an embodiment has been described. However, the configurations of the detection system 1, the detection device 2, and the detection method are not limited to the embodiment. For example, the detection device 2 may include only the AE sensor 41 attached to the trough rib 23, and may not include the AE sensor 42 attached to the deck plate 21. Each of the position orientator 81, the threshold setter 82, and the deterioration diagnoser 83 of the deterioration detector 72 may be a software function portion which is realized by the processor (for example, a CPU) of the information processing device 4 by executing a program, or may be a hardware function portion such as an LSI. In addition, in the detection device 2, the BPF 33 and ADC 34 may be formed as a portion of the signal processor 35.

According to at least an embodiment described above, the detection device is used for a structure including a first member that supports, from below, a traveling surface on which a vehicle travels, a second member provided on an opposite side of the traveling surface with respect to the first member, and a welded portion that is provided along an end of the second member facing the first member and fixes the first member and the second member in a continuous manner in a longitudinal direction of the second member. The detection device includes a plurality of AE sensors and an outputter. The plurality of the AE sensors are disposed so as to be spaced apart from each other in a direction in which the welded portion extends, and detect an elastic wave transmitted to the second member while the AE sensors are attached to the second member. The outputter outputs information, obtained from outputs of the plurality of the AE sensors. According to such a configuration, it is possible to easily detect a crack occurring in the structure.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A detection device that is used for a structure, the structure including:
    a first member that supports, from below, a traveling surface on which a vehicle travels;
    a second member provided on an opposite side of the traveling surface with respect to the first member; and
    a welded portion that is provided along an end of the second member facing the first member, the welded portion fixing the first member and the second member in a continuous manner in a longitudinal direction of the second member,
the detection device comprising:
    a first plurality of acoustic emission sensors that are disposed so as to be spaced apart from each other in a direction in which the welded portion extends and are configured to detect an elastic wave transmitted to the second member, each acoustic emission sensor being attached to the second member; and
    an outputter that outputs information, obtained from outputs of the first plurality of the acoustic emission sensors.

2. The detection device according to claim 1, wherein the second member includes a plate portion extending in a direction away from the traveling surface, and
the first plurality of the acoustic emission sensors are attached to the plate portion of the second member and are configured to detect the elastic wave transmitted to the plate portion.

3. The detection device according to claim 1, wherein where $\theta$ denotes an angle between a line connecting any given two adjacent acoustic emission sensors of the first plurality of the acoustic emission sensors and a reference line extending in the direction in which the welded portion extends, the following relationship is satisfied:

$$-20 \text{ degrees} < \theta < 20 \text{ degrees}.$$

4. The detection device according to according to claim 1, further comprising a second plurality of acoustic emission sensors that are disposed so as to be spaced apart from each other in the direction in which the welded portion extends and are configured to detect an elastic wave transmitted to the first member, each acoustic emission sensor being attached to the first member,
wherein the outputter outputs information, obtained from outputs of the first plurality of the acoustic emission sensors attached to the second member and the second plurality of the acoustic emission sensors attached to the first member.

5. The detection device according to according to claim 1, further comprising
    an extractor that extracts information relating to characteristics of the elastic wave obtained by each of the first plurality of acoustic emission sensors, based on a detection result of the acoustic emission sensor, wherein
the outputter outputs information relating to the characteristics of the elastic wave obtained by the acoustic emission sensor and extracted by the extractor and information relating to an arrival time of the elastic wave at the acoustic emission sensor in association with each other.

6. The detection device according to claim 1, wherein the second member is a trough rib.

7. The detection device according to claim 1, wherein the second member has a substantially U-shaped cross-sectional shape.

8. The detection device according to claim 1, wherein the second member includes a first plate portion and a second plate portion,
- the first plate portion and the second plate portion are inclined with respect to each other so that a distance between the first plate portion and the second plate portion gradually decreases as the first plate portion and the second plate portion extend away from the traveling surface,
- the welded portion connects a lower surface of the first member and upper ends of the first plate portion and the second plate portion, and
- the first plurality of acoustic emission sensors are attached to the first plate portion of the second member.

9. A detection system configured to detect a state of a structure,
the structure including:
- a first member that supports, from below, a traveling surface on which a vehicle travels;
- a second member provided on an opposite side of the traveling surface with respect to the first member; and
- a welded portion that is provided along an end of the second member facing the first member, the welded portion fixing the first member and the second member in a continuous manner in a longitudinal direction of the second member, the detection system comprising:
- a first plurality of acoustic emission sensors that are disposed so as to be spaced apart from each other in a direction in which the welded portion extends and are configured to detect an elastic wave transmitted to the second member, each acoustic emission sensor being attached to the second member; and
- a position determiner configured to determine a generation source position of the elastic wave, based on information obtained from outputs of the first plurality of the acoustic emission sensors.

10. The detection system according to claim 9, wherein the first plurality of the acoustic emission sensors include a third acoustic emission sensor and a fourth acoustic emission sensor,
and
the position determiner is configured to determine the generation source position of the elastic wave based on a time difference between arrival times of the elastic waves at the third acoustic emission sensor and the fourth acoustic emission sensor, a propagation velocity of the elastic wave in the second member, and a position of the welded portion.

11. The detection system according to claim 10, wherein in a case where similarity between characteristics of the elastic wave in the third acoustic emission sensor and characteristics of the elastic wave in the fourth acoustic emission sensor is in a predetermined range, the position determiner determines that the elastic wave detected by the third acoustic emission sensor and the elastic wave detected by the fourth acoustic emission sensor are the same elastic wave, and determines a generation source position of the elastic wave.

12. The detection system according to claim 9, further comprising
a determiner configured to determine a state of deterioration of the structure based on information relating to a density of generation source positions of elastic waves which are obtained by accumulating information of the generation source position of the elastic wave determined by the position determiner.

13. The detection system according to claim 9, wherein the second member is a trough rib.

14. The detection system according to claim 9, wherein the second member has a substantially U-shaped cross-sectional shape.

15. The detection system according to claim 9, wherein the second member includes a first plate portion and a second plate portion,
- the first plate portion and the second plate portion are inclined with respect to each other so that a distance between the first plate portion and the second plate portion gradually decreases as the first plate portion and the second plate portion extend away from the traveling surface,
- the welded portion connects a lower surface of the first member and upper ends of the first plate portion and the second plate portion, and
- the first plurality of acoustic emission sensors are attached to the first plate portion of the second member.

16. A detection method of detecting a state of a structure, the structure including:
- a first member that supports, from below, a traveling surface on which a vehicle travels;
- a second member provided on an opposite side of the traveling surface with respect to the first member; and
- a welded portion that is provided along an end of the second member facing the first member, the welded portion fixing the first member and the second member in a continuous manner in a longitudinal direction of the second member, the detection method comprising:
determining a generation source position of the elastic wave based on results of detection of elastic waves transmitted to the second member at a plurality of positions spaced apart from each other in a direction in which the welded portion extends, the results of detection being output from a first plurality of acoustic emission sensors.

17. The detection method according to claim 16, wherein the second member is a trough rib.

18. The detection method according to claim 16, wherein the second member has a substantially U-shaped cross-sectional shape.

19. The detection method according to claim 16, wherein the second member includes a first plate portion and a second plate portion,
- the first plate portion and the second plate portion are inclined with respect to each other so that a distance between the first plate portion and the second plate portion gradually decreases as the first plate portion and the second plate portion extend away from the traveling surface,
- the welded portion connects a lower surface of the first member and upper ends of the first plate portion and the second plate portion, and
- the first plurality of acoustic emission sensors are attached to the first plate portion of the second member.

* * * * *